United States Patent [19]
Greenstein

[11] Patent Number: 5,827,063
[45] Date of Patent: Oct. 27, 1998

[54] METHOD OF MAKING DENTAL RESTORATION EMPLOYING PREFORMS

[76] Inventor: Jean Greenstein, 5339 Lindley Ave., Apt. 303, Tarzana, Calif. 91356

[21] Appl. No.: 835,225

[22] Filed: Apr. 7, 1997

[51] Int. Cl.⁶ .................................................. A61C 11/00
[52] U.S. Cl. .......................... 433/213; 433/214; 433/223; 264/19
[58] Field of Search ..................... 433/213, 214, 433/218, 223, 226, 202.1

[56] References Cited

U.S. PATENT DOCUMENTS

| | | | |
|---|---|---|---|
| 833,883 | 10/1906 | Lentz | 433/213 |
| 2,930,124 | 3/1960 | Pos | 433/223 |
| 3,058,216 | 10/1962 | Cohen | 433/223 |
| 3,102,337 | 9/1963 | Mintz | 433/223 |
| 3,224,050 | 12/1965 | Redtenbacher | 433/213 |
| 3,375,582 | 4/1968 | Myerson | 433/223 |
| 3,457,644 | 7/1969 | Susman et al. | 433/213 |
| 3,561,119 | 2/1971 | Susman et al. | 433/213 |
| 3,566,469 | 3/1971 | Pelizzari | 433/213 |
| 3,628,248 | 12/1971 | Kroder et al. | 433/175 |
| 3,971,133 | 7/1976 | Mushabac | 433/213 |
| 4,078,310 | 3/1978 | Horger, Jr. | 433/213 |
| 4,380,435 | 4/1983 | Raeder et al. | 433/180 |
| 4,398,887 | 8/1983 | Balde et al. | 433/218 |
| 4,562,882 | 1/1986 | Alleluia | 164/529 |
| 4,681,543 | 7/1987 | Monroy | 433/196 |
| 4,828,117 | 5/1989 | Panzera et al. | 206/63.5 |
| 4,881,898 | 11/1989 | Harvey, Sr. et al. | 433/215 |
| 4,952,151 | 8/1990 | Metcalfe | 433/223 |
| 5,201,657 | 4/1993 | Koukos | 433/213 |
| 5,342,201 | 8/1994 | Oden | 433/223 |
| 5,346,397 | 9/1994 | Braiman | 433/223 |

FOREIGN PATENT DOCUMENTS

3731805 A1  3/1989  Germany.
62-64358   3/1987  Japan.

*Primary Examiner*—John J. Wilson
*Attorney, Agent, or Firm*—Cummings & Lockwood

[57] ABSTRACT

A method of making a dental restoration is provided wherein preforms based on impressions of actual human teeth of varying sizes are employed. The method consistently yields dental restorations having excellent aesthetics and does not demand a high level of technical and artistic skill of the individual dental technician.

9 Claims, 4 Drawing Sheets

METHOD OF MAKING DENTAL RESTORATION EMPLOYING PREFORMS

FIELD OF THE INVENTION

This invention relates to a method of making dental restorations wherein dental restorations possessing consistently excellent aesthetics can be produced in a short period of time. More particularly, this invention relates to a method wherein preforms of ideal tooth structures are employed.

BACKGROUND OF THE INVENTION

Many different techniques for fabricating dental restorations such as inlays, onlays, crowns, bridges, and the like, are known. These include the direct lift technique, the refractory cast technique and the castable/pressable ceramics method. For a general description of these methods, reference may be had to U.S. Pat. No. 4,940,676. However, fabricating a dental restoration is a time consuming procedure regardless of what particular fabricating method is employed since each method demands a considerable amount of technical and artistic skill of the individual dental technician who fabricates the restoration. An all-ceramic restoration such as a crown or bridge will typically take a dental technician of average skill from 1 to 3 hours to fabricate. This is because the dental technician must employ successive build-up/firing operations to form the restoration. How well the final dental restoration duplicates the appearance of natural dentition often depends on how artistic the dental technician is and how technically accurate his/her understanding of tooth structure is. Furthermore, since the level of skill and experience among dental technicians varies significantly throughout the dental industry, there is no uniformity in quality of dental restorations throughout the industry.

The use of preforms which generally duplicate the shape and appearance of natural teeth in the fabrication of dental restorations is generally known. See, e.g., U.S. Pat. Nos. 3,058,216, 3,102,337, 3,375,582, 3,457,644, 3,561,119, 3,566,469 and 3,971,133. However, the inventor is aware of no patent which discloses preforms of tooth structures derived from actual teeth of children and adults.

It is an object of the present invention to provide a method of making dental restorations which does not demand a high level of technical and artistic skill of the individual dental technician who fabricates dental restorations in order to achieve consistent, excellent aesthetics.

It is a further object of the present invention to provide a method of making highly aesthetic dental restorations which can be conducted in a short period of time with a minimum amount of technical and artistic skill.

It is an even further object of the present invention to provide a method of making highly aesthetic dental restorations which provides reproducible results.

SUMMARY OF THE INVENTION

In accordance with these and further objects of the invention, a method for making a dental restoration is provided which comprises:
  providing a preform of a tooth structure;
  appending the preform to a model of a prepared tooth to form a temporary model of a natural tooth;
  taking an impression of the temporary model to form an index;
  cutting back the temporary model to form a base;
  reproducing the base in porcelain or resin;
  building up incisal porcelain or resin on the base;
  pressing the index down on the incisal porcelain or resin and hardening the incisal porcelain or resin to provide the dental restoration.

The term "preform" utilized herein shall be understood to refer to a prefabricated replica of a natural tooth and/or labial, lingual and/or occlusal portion of a natural tooth. The preforms precisely duplicate the appearance of actual human teeth, i.e., the preforms are obtained by taking impressions of actual teeth of children and/or adults of varying sizes.

DESCRIPTION OF THE PREFERRED EMBODIMENTS

Figure 1:
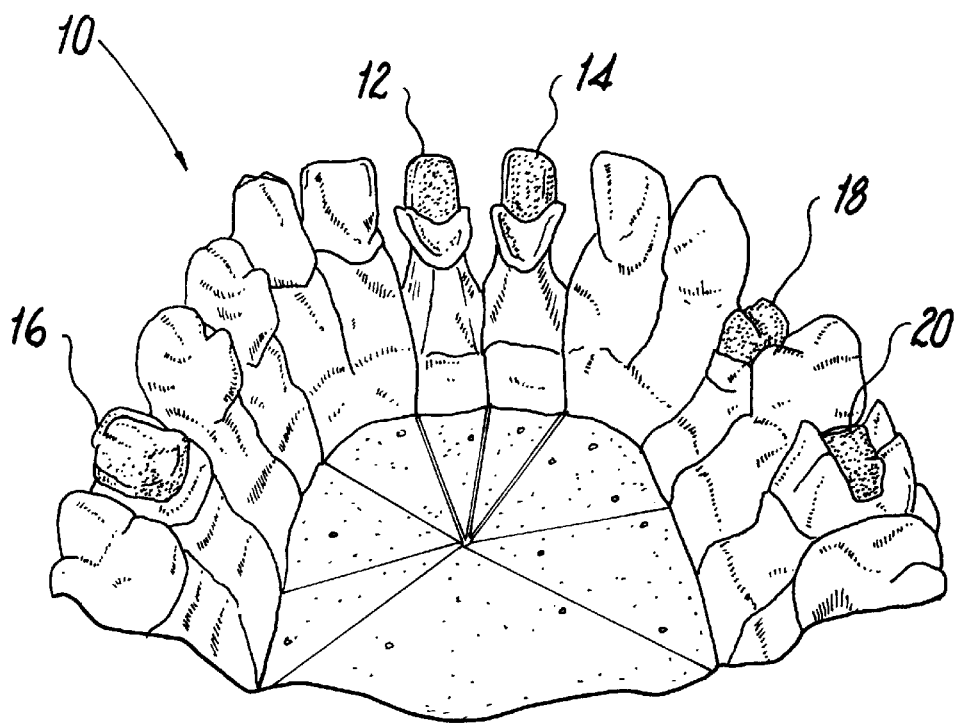
Figure 2:
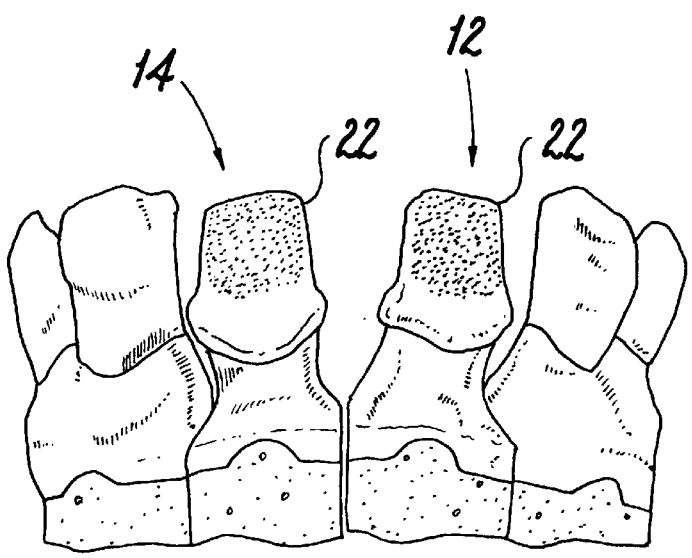

In accordance with this invention, a patient's tooth (or teeth) to be restored (cosmetically or otherwise) is prepared by well known procedures, e.g., the tooth is ground to form a stump or facing which provides adequate space for the restoration, and a model of the patient's teeth of the upper and/or lower jaw, including the prepared tooth, is prepared from gypsum or other suitable material in accordance with well known procedures. Such a model is depicted generally at 10 in FIG. 1. FIG. 1 depicts several prepared teeth, i.e., at 12, 14, 16, 18 and 20. As shown in FIG. 1, the model is cut to form dies of the individual prepared teeth so that a die of each prepared tooth can be conveniently separated from the model of the patient's teeth. FIGS. 2–7 depict anterior teeth whereas FIGS. 8–12 depict a posterior molar. It should be understood that the drawings are for illustrative purposes only and that the invention is equally applicable to other tooth anatomies as well.

The preforms utilized herein are preferably formed as follows: impressions of healthy teeth of all sizes of children and/or adults are taken utilizing well known techniques and materials; positive models of these teeth are formed utilizing well known techniques and materials; to correct slight defects and/or imperfections (if present), molten wax or other suitable material is optionally incorporated onto the surfaces of the positive models and/or the positive models are custom hand carved to render perfect tooth anatomies and function; impressions of the positive models are taken and preforms of teeth having perfect or ideal tooth anatomies are obtained from the impressions of the positive models. Preferably, wax is employed herein to fabricate the preforms. Since the preforms utilized herein are derived from actual healthy teeth of children and adults, i.e., the preforms are obtained by taking impressions of actual teeth of children and/or adults of varying sizes, the preforms precisely duplicate the labial, lingual and/or occlusal surfaces of natural dentition. Preforms are thus provided in a wide range of sizes for each type of tooth anatomy.

Figure 3:
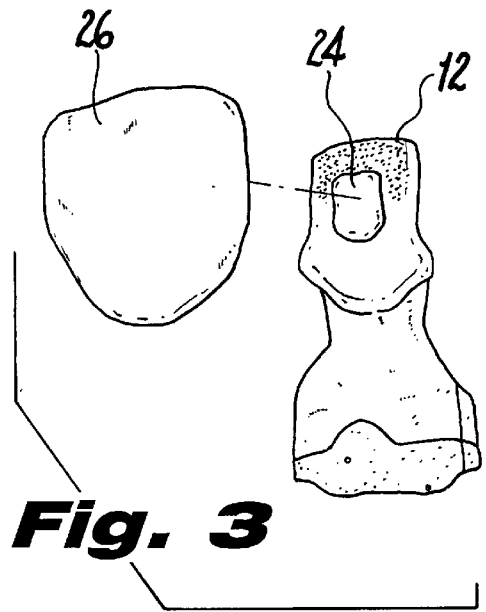
Figure 4:
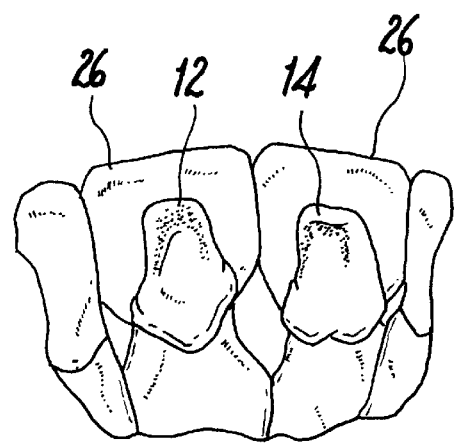
Figure 7:
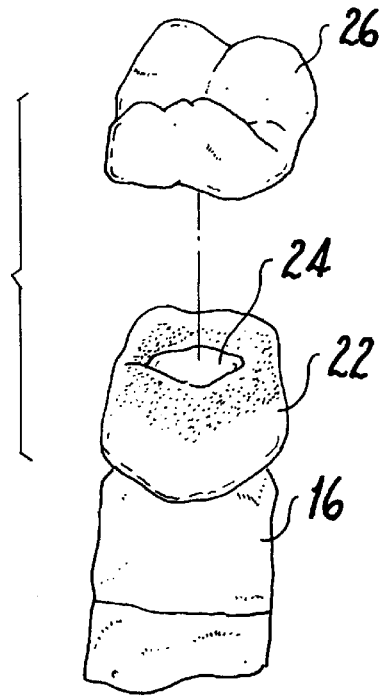
Figure 8:
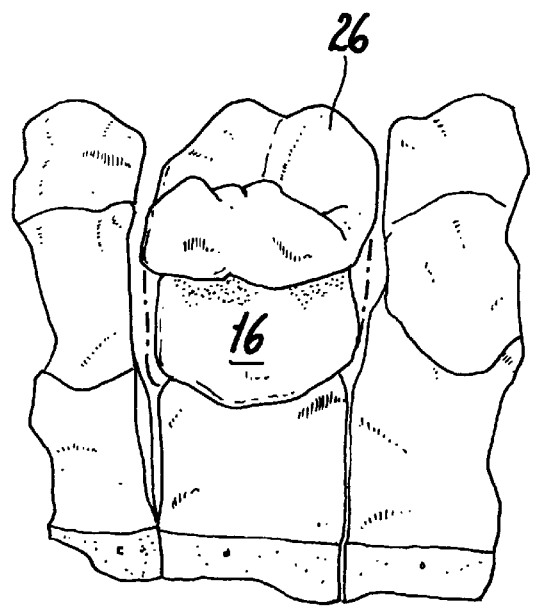

The periphery of margins on the die of the prepared tooth is preferably marked with colored marking pencil and the die is lubricated with separating medium as is well known in order to facilitate separation of a restoration from the die. The die is then dipped in hot wax to form a thin uniform wax skin (depicted at 22 in FIG. 2) on the die model. Thereafter, as shown in FIGS. 3 (anterior) and 7 (posterior), a small amount of soft utility wax 24 is placed on the die. Preform 26, preferably made of wax, of the appropriate size and anatomy is gently pressed against the soft utility wax to thereby append the preform to the model to form the temporary model of a natural tooth. FIGS. 3 and 7 depict preform 26 prior to being appended to the die model and FIGS. 4 and 8 depict wax preform 26 after being appended to the die model. After being appended to the die, preform 26 is positioned for correct alignment with other teeth and checked for correct bite.

Figure 5:
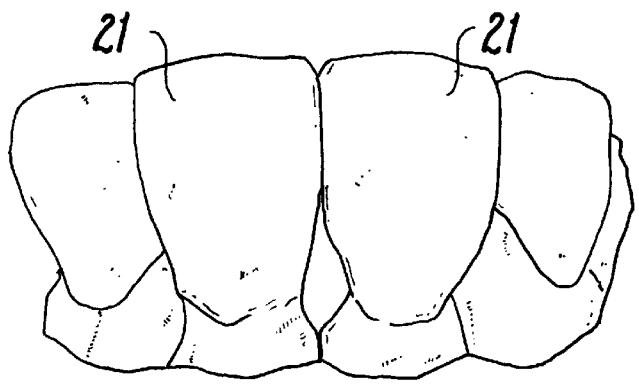
Figure 6:
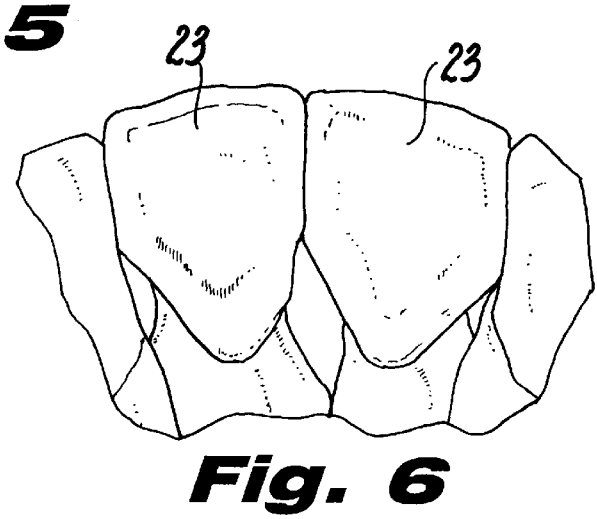
Figure 9:
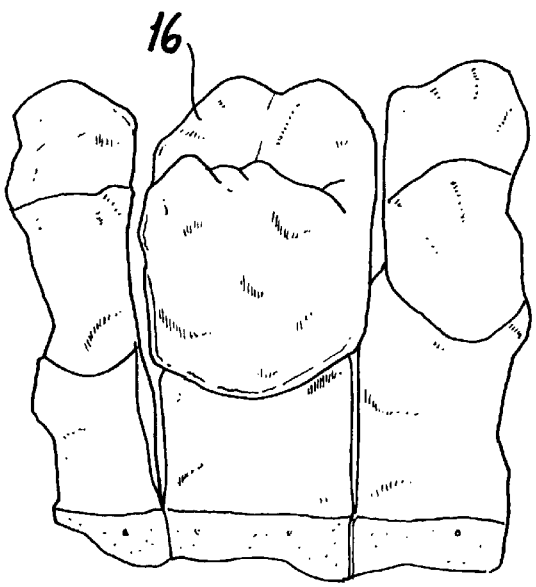

In some cases, after appending the preform to the die, it may be necessary to manually build up additional wax or other suitable material to complete the temporary model. The dotted lines shown in FIG. 8 indicate those areas which will be built up with molten wax or other suitable material in order to complete the temporary restoration. This procedure normally takes a few seconds or minutes to perform and does not require any special skill of the dental technician. A heated dropper connected to a supply of molten wax can be used for this purpose. Such devices are well known and permit the user to accurately dispense small quantities of molten wax in small surface areas and crevices, e.g., those surrounding the tooth margin. The wax quickly solidifies to provide a complete reproduction of the tooth in wax. FIG. 5 depicts the labial sides 21 of the temporary models of the anterior teeth and FIG. 6 depicts the lingual sides 23 of the temporary models after additional wax has been build up around the gingival margins to complete the temporary model. FIG. 9 depicts the complete temporary model for the posterior molar. It will be readily appreciated that the preforms utilized in the practice of this invention substantially reduce the amount of time and skill required to duplicate the appearance of natural teeth.

Figure 10:
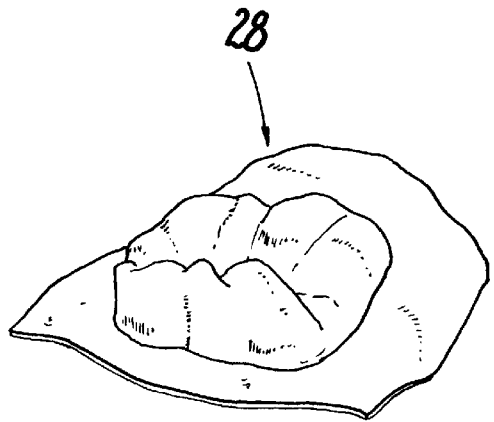

After the temporary model of the tooth has been thus formed, an impression of the temporary model is taken to form an index such as index 28 shown in FIG. 10. The impression can be taken of the labial, lingual and/or occlusal surface of the tooth. The impression can be taken with any suitable impression-taking material known in the art. The index is removed and set aside.

Thereafter, the temporary model is cut back according to the appropriate incisal size to form a base which will be reproduced in porcelain or resin. The base represents the dentine layer of a natural tooth. It is of course well known by those skilled in the art that teeth comprise an inner dentine layer and an outer enamel layer. Dental restorations typically comprise several layers of porcelain and/or resin to simulate the dentine and enamel layers of natural teeth. To simulate the dentine layer of natural teeth, a layer of body porcelain is employed. Body porcelains exhibit translucence to a degree similar to that of the dentine layer of natural dentition. To simulate the appearance of the enamel layer of a natural tooth, a layer of incisal porcelain is disposed on the layer of body porcelain. Incisal porcelains approach the translucency of the enamel layer of natural dentition. The thickness of the body and incisal layers vary over the surface of the restoration so that the color of the restoration, like natural teeth, will likewise vary over its surface. Thus, the wax reproduction is cut back (not shown) with a knife or other suitable instrument to accommodate the incisal layer of the dental restoration. This procedure is well within the skill of the ordinary skilled dental technician.

The base is then lifted off the die and reproduced in body porcelain or resin in accordance with any well known technique. In accordance with a preferred embodiment, the base is removed from the die and invested or surrounded by a mix of plaster-like material which is allowed to harden. A channel or opening leads from the outer surface of the investment into the wax pattern. The invested pattern is placed in an oven where the wax is eliminated through the opening. A casting or pressure machine melts a mass of porcelain material and casts it into the opening of the investment. The molten porcelain is allowed to harden to assume the shape of the former base pattern. After cooling, the hardened body porcelain is separated from the investment to provide a reproduction of the base.

In accordance with another preferred embodiment, a resin can be employed to reproduce the base as follows: after removing the wax base from the model, the model is again lubricated with separating agent and pre-polymerized dental resin having a putty-like consistency is applied to the model by hand. The dental resin is molded to approximate the shape and configuration of the base and then lifted from the model and cured using suitable means, i.e., heat, light, pressure, vacuum, combinations thereof, and the like. It will be understood that the dental resin can be reinforced with any suitable material, e.g., short or long organic or inorganic fibers or particles.

Figures 11, 12:
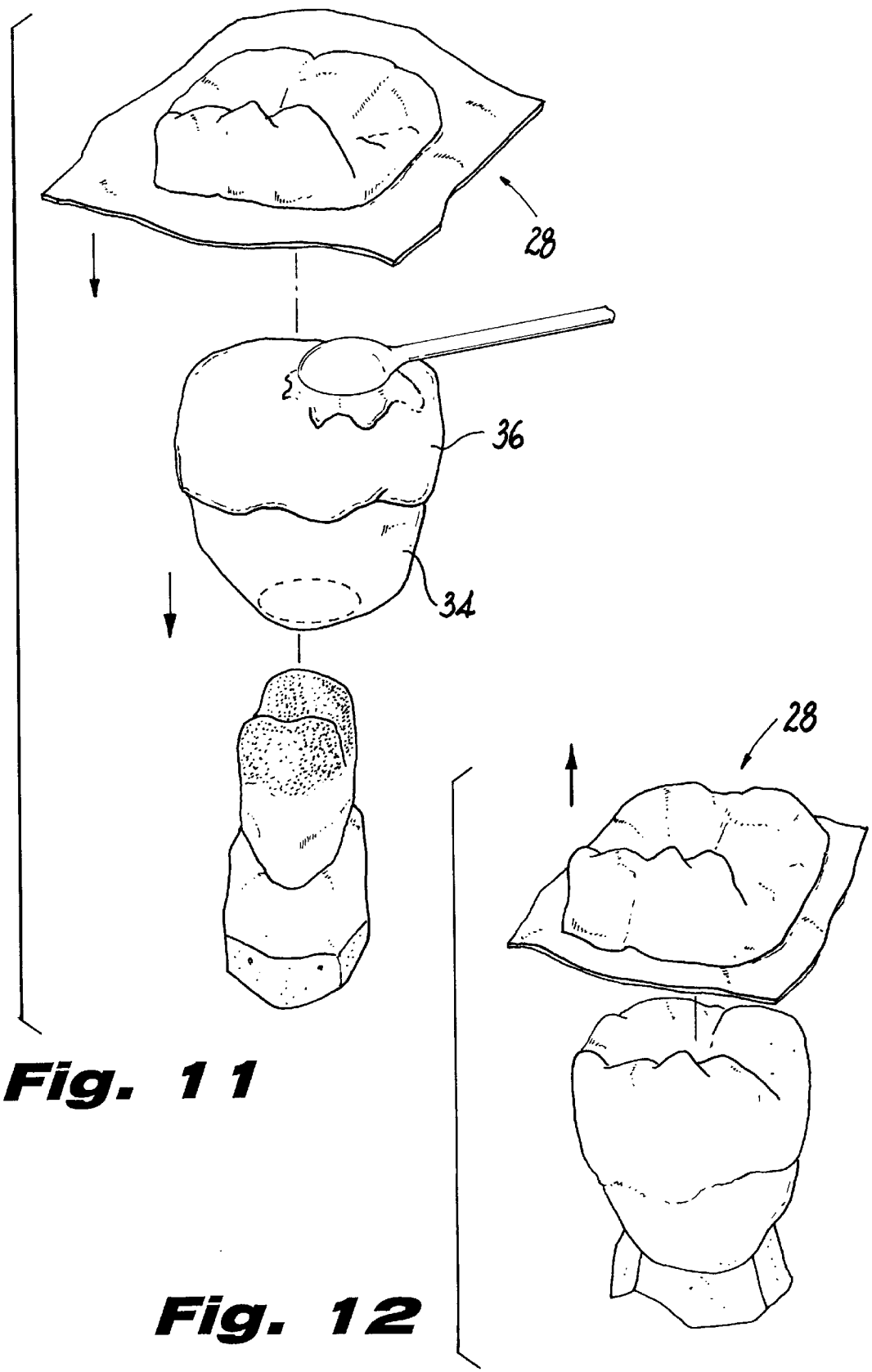

The reproduction of the base, for example base 34 depicted in FIG. 11, is placed onto the original model. Powdered incisal porcelain is mixed with a suitable liquid, e.g., water, to form a slurry, shown at 36 in FIG. 11, which is built up on the occlusal surface of the base. Alternatively, resin can be utilized for this purpose. As further shown in FIG. 11, previously formed index 28 is then pressed down on the incisal porcelain or resin, thereby recreating the original labial, lingual and/or occlusal anatomy with all of its contours and complex surface characteristics as shown in FIG. 12. The incisal porcelain or resin is then hardened by suitable means, e.g., heat, light, chemical initiation, combinations of these, and the like. It will be understood that color may be imparted to the body and incisal layers by adding conventional pigments thereto.

It will be readily apparent to those skilled in the art that the method of this invention can be performed quickly with a minimum amount of technical or artistic skill. The method will consistently yield highly aesthetic dental restorations which can barely be differentiated from natural teeth.

The above-described method can be applied in the formation of a wide variety of dental restorations, including inlays, onlays, crowns, bridges, and the like. The materials used to fabricate the final dental restorations can be selected from a wide variety of conventional dental porcelains and resins.

While this invention has been disclosed herein in connection with certain embodiments and certain procedural details, it is clear that changes, modifications or equivalents can be used by those skilled in the art. For example, the preforms of this invention can be fabricated out of resin or porcelain as opposed to wax. Accordingly, such changes within the principles of this invention are intended to be included within the scope of the claims below.

What is claimed is:

1. A method of making a dental restoration which comprises:

providing a preform of a tooth structure;
   appending the preform to a model of a prepared tooth to form a temporary model of a natural tooth;
   taking an impression of the temporary model to form an index;
   cutting back the temporary model to form a base;
   reproducing the base in body porcelain or resin;
   building up incisal porcelain or resin on the base;
   pressing the index down on the incisal porcelain or resin and hardening the incisal porcelain or resin to provide the dental restoration.

2. The method of claim 1 wherein the preform is fabricated out of wax.

3. The method of claim 1 wherein the preform is based on an impression of a human tooth.

4. The method of claim 1 wherein prior to taking an impression of the temporary model, wax is manually built up on the temporary model to complete the temporary model.

5. The method of claim 1 wherein the tooth structure comprises a labial, lingual and/or occlusal surface of an anterior or posterior tooth.

6. The method of claim 1 wherein the step of hardening the incisal porcelain or resin comprises heating the incisal porcelain or resin.

7. The method of claim 1 wherein the dental restoration is fabricated entirely out of porcelain.

8. The method of claim 1 wherein the dental restoration is fabricated entirely out of resin.

9. The method of claim 1 wherein the dental restoration is selected from the group consisting of a crown, bridge, inlay and onlay.

* * * * *